US007211261B1

(12) United States Patent
Moyer et al.

(10) Patent No.: US 7,211,261 B1
(45) Date of Patent: May 1, 2007

(54) STABLE LIQUID FORMULATIONS OF BOTULINUM TOXIN

(75) Inventors: Elizabeth Moyer, Mill Valley, CA (US); Pamela Hirtzer, Piedmont, CA (US)

(73) Assignee: Solstice Neurosciences, Inc., Malvern, PA (US)

( * ) Notice: Subject to any disclaimer, the term of this patent is extended or adjusted under 35 U.S.C. 154(b) by 0 days.

(21) Appl. No.: 09/393,590

(22) Filed: Sep. 9, 1999

Related U.S. Application Data

(60) Provisional application No. 60/099,870, filed on Sep. 11, 1998.

(51) Int. Cl.
*A61K 39/02* (2006.01)
*A61K 39/08* (2006.01)

(52) U.S. Cl. .............................. 424/236.1; 424/234.1; 424/239.1; 424/247.1

(58) Field of Classification Search ............. 424/236.1, 424/239.1, 184.1, 234.1, 832; 530/350, 806, 530/825, 820; 514/2, 12
See application file for complete search history.

(56) References Cited

U.S. PATENT DOCUMENTS

| | | | |
|---|---|---|---|
| 4,932,936 A | 6/1990 | Dykstra et al. | |
| 5,053,005 A | 10/1991 | Borodic et al. | |
| 5,183,462 A | 2/1993 | Borodic | |
| 5,437,291 A | 8/1995 | Pasricha et al. | |
| 5,512,547 A | 4/1996 | Johnson et al. | |
| 5,562,899 A | 10/1996 | Gerber | |
| 5,696,077 A | 12/1997 | Johnson et al. | |
| 5,714,468 A | 2/1998 | Binder | |
| 5,721,215 A | 2/1998 | Aoki et al. | |
| 5,766,605 A | 6/1998 | Sanders et al. | |
| 6,113,915 A | 9/2000 | Aoki et al. | ............... 424/236.1 |
| 6,139,845 A | 10/2000 | Donovan | ................. 424/236.1 |
| 6,146,902 A * | 11/2000 | McMaster | .................... 436/177 |
| 6,350,455 B1 | 2/2002 | Donovan | ................. 424/239.1 |
| 6,358,513 B1 | 3/2002 | Voet et al. | ............... 424/239.1 |

FOREIGN PATENT DOCUMENTS

| | | |
|---|---|---|
| EP | 0 593 176 A2 | 4/1994 |
| WO | WO 93/05800 | 4/1993 |
| WO | WO 95/17904 | 7/1993 |
| WO | WO 94/00481 | 1/1994 |
| WO | WO 94/28922 | 12/1994 |
| WO | WO 94/28923 | 12/1994 |
| WO | WO 95/05842 | 3/1995 |
| WO | WO 95/17904 | 7/1995 |
| WO | WO 95/28171 | 10/1995 |
| WO | WO 95/30431 | 11/1995 |
| WO | WO 95/03041 | 2/1996 |
| WO | WO 96/11699 | 4/1996 |
| WO | WO 96/39167 | 12/1996 |
| WO | WO 97/35604 | 10/1997 |

OTHER PUBLICATIONS

Schwarz W. Archiv. fur lebensmittelhygiene 30: 1-40, pp. 29-33, 1979 (original & translated material).*
Schantz and Johnson. In: Therapy with Botulinum Toxin. (Ed) J. Jankovic et al. Marcel Dekker, Inc. New York, 41-49, 1994.*
Grethlein et al. Pain Med. 2: #203, p. 239, 2001.*
Saprykina et al. Zh. Mikrobiol. Epidermol. Immunobiol. 9: 86-91, 1980.*
Webster's II Riverside University Dictionary, The Riverside Publishing Company, p. 1032, 1984.*
Schantz and Sugiyama. J. Agr. Food Chem. 22: 26-30, 1974.*
Gimenez et al. Appl. Environ. Microbiol. 53: 2827-2830, 1987.*
Sloop et al. Neurology 48: 249-253, 1997.*
Schantz et al. Perspect. Biol. Med. 40 (3) Spring, 317-327, 1997.*
Moyer et al. In: Therapy with Botulinum Toxin. (Ed) J. Jankovic et al. Marcel Dekker, Inc. New York, pp. 71-85, 1994.*
Uvarova et al. Zhurnal Mikrobiologii, Epidemiologii i Immunobiologii 11: 42-46, 1980—English abstract.*
McLellan et al., Therapeutic botulinum type A toxin: factors affecting potency, Toxicon, 1996, vol. 34, No. 9, pp. 975-985. See IDS filed Apr. 25, 2006, p. 3 of 4.*
Gartlan et al., Crystalline preparation of botulinum toxin type A (Botox): degradation in potency with storage, Otolaryngol Head Neck Surg. Nov. 1993, vol. 108, No. 2, pp. 135-140. See IDS filed Apr. 25, 2006, p. 3 of 4.*
Goodnough et al. Stabilization of Botulinum Toxin Type A during Lyophilization, Applied and Environmental Microbiology, Oct. 1992, 3426-3428. See IDS filed Apr. 25, 2006, p. 4 of 4.*
First, E.R., et al., "Dose Standardisation of Botulinum Toxin," The Lancet, vol. 343. p. 1035, ( Apr. 23, 1994).
Gartlan, M.G., et al., "Crystalline preparation of botulinum toxin type A (Botox): Degradation in potency with storage," Otolaryngology, vol. 108, p. 135-140, (1993).
Hambleton, B.C., et al., "Production, Purification and Toxoiding of *Clostridium botulinum* Type A Toxin," Biomedical Aspects of Botulism, Academic Press (US), p. 247-260, (1981).
Kadis, S., et al., "Microbial Toxins," Bacterial Protein Toxins, Academic Press (US), p. 1-68, (1971).
Lamanna, C., et al., "The Isolation of Type B Botulinum Toxin," Journal of Bacteriology, (US), vol. 54, p. 575-584, (1947).
Melling, J., et al., "*Clostridium botulinum* Toxins: Nature and Preparation for Clinical Use," Eye, vol. 2, p. 16-23, (1988).
Schantz, E.J., et al., "Microbiological Methods," Journal of the AOAC (UK), Association of Official Analytical Chemists, vol. 61 ( No. 1), p. 96-99, (1978).

(Continued)

*Primary Examiner*—Brenda Brumback
*Assistant Examiner*—Sharon Hunt
(74) *Attorney, Agent, or Firm*—Albert P. Halluin; Lien-Chi Nguyen; Wilson Sonsini Goodrich & Rosati

(57) ABSTRACT

The invention includes liquid formulations of botulinum toxin that are stable to storage in liquid form at standard refrigerator temperatures for at least 1–2 years and to storage at higher temperatures for at least 6 months. The invention also includes methods of treatment using such formulations for various therapeutic and cosmetic purposes.

35 Claims, No Drawings

OTHER PUBLICATIONS

Schantz, E.J., et al., "Quality of Botulinum Toxin For Human Treatment," Botulinum and Tetanus Neurotoxins, B.R. Dasgupta, ed., Plenum Press, p. 657-659, (1993).

Sloop, R.R., MD, et al., "Human response to botulinum toxin injection: Type B compared with type A,", The American Academy of Neurology (US), vol. 49, p. 189-194, ( Jul. 27, 1997).

Sugii, S., et al., "Correlation Between Oral Toxicity and In Vitro Stability of *Clostridium botulinum* Type A and B Toxins of Different Molecular Sizes," Infection and Immunity, American Society of Microbiology (US), vol. 16, p. 910-914, (1977).

Wright, G.P., "The Neurotoxins of *Clostridium botulinum* and *Clostridium tetani*," Pharmacology, vol. 7, p. 413-465, (1955).

Schantz, E.J., et al., "Dose standardisation of botulinum toxin," The Lancet, vol. 335, p. 421, ( 1994).

Tsui, J.K.C., et al., "Botulinum toxin type B in the treatment of cervical dystonia: A pilot study," Neurology, vol. 45, p. 2109-2110, (1995).

Moyer, E.D. et al., "Effects of Intramuscular Injection of Botulinum Toxin Type B in Nonhuman Primates," Botulinum and Tetanus Neurotoxins, Plenum Press (US), p. 655-656, (1993).

Lew, M.F. et al., "Botulinum toxin type B: A double-blind, placebo-controlled, safety and efficacy study in cervical dystonia" Neurology (US), vol. 49, p. 701-707, (1997).

Prevot, A.R. et al., "New Studies of Botulism and its Five Toxin Types," Annals of the Pasteur Institute (FR), vol. 85, p. 2-20, (1953).

Simpson, Lance L. "Botulinum Toxin: A Deadly Poison Sheds Its Negative Image" *Annals of Internal Medicine*, 125:616-617, Oct. 1, 1996.

Henry S. Sacks et al, *Clostridium botulinum* Type E Toxin: Effect of pH and Method of Purification on Molecular Weight, Applied Microbiology, Sep. 1974, p. 374-382, vol. 28:3, American Society for Microbiology, USA.

Iwao Ohishi et al, Purification of *Clostridium botulinum* Type F Progenitor Toxin, Applied Microbiology, Dec. 1974, p. 923-928, vol. 28:6, American Society for Microbiology, USA.

Iwao Ohishi et al, Molecular Construction of *Clostridium botulinum* Type F Progenitor Toxin, Applied Microbiology, Apr. 1975, p. 444-447, vol. 29:4, American Society for Microbiology, USA.

Shunji Sugii et, Correlation Between Oral Toxicity and In Vitro Stability of *Clostridium botulinum* Type A and B Toxins of Different Molecular Sizes, Infection and Immunity, Jun. 1977, p. 910-914, vol. 16:3, American Society for Microbiology, USA.

Iwao Ohishi et al, Activation of Botulinum Toxins in the Absence of Nicking, Infection and Immunity, Aug. 1977, p. 402-407, vol. 17:2, American Society for Microbiology, USA.

Albert L. Lehiniger, The Molecular Basis of Cell Structure and Function, Biochemistry (Second Edition), Jul. 1978, 45-50, Worth Publishers, Inc., New York, USA.

Iwao Ohishi et al, Oral Toxicities of *Clostridium botulinum* Type C and D Toxins of Different Molecular Sizes, Infection and Immunity, May 1980, p. 303-309; vol. 28:2.

Iwao Ohishi et al, Purification and Characterization of Two Components of Botulinum $C_2$ Toxin, Infection and Immunity, Dec. 1980, p. 668-673, vol. 30:3.

Leon Lachman, Ph.D. et al, The Theory and Practice of Industrial Pharmacy, third edition, 1986, p. 458-460, Lea & Febiger, Philadelphia, USA.

Flora Chen et al, Biophysical Characterization of the Stability of the 150-Kilodalton Botulinum Toxin, the Nontoxic Component, and the 900-Kilodalton Botulinum Toxin Complex Species, Infection and Immunity, Jun. 1988, p. 2420-2425, vol. 66:6, American Society of Microbiology, USA.

J. Melling et al., *Clostridium botulinum* Toxins: Nature and Preparation for Clinical Use; Eye, 1988:2, p. 16-23.

J. Halouzka et al, Effect of pH on the Stability of Type-C Toxin of *Clostridium botulinum*, Folia Microbiol, 1992, p. 157-158, vol. 37:2.

Giampietro Schiavo et al, Botulinum G Neurotoxin Cleaves VAMP/Synaptobrevin at a Single Ala-Ala Peptide Bond, The Journal of Biological Chemistry, Aug. 12, 1994, p. 20213-20216, vol. 269:32, The American Society for Biochemistry and Molecular Biology, Inc., USA.

Rossella Pellizzari et al, Structural Determinants of the Specificity for Synaptic Vesicle-associated Membrane Protein/Synaptobrevin of Tetanus and Botulinum Type B and G Neurotoxins, The Journal of Biological Chemistry, Aug. 1996, p. 20353-20358, vol. 271:34, The American Society for Biochemistry and Molecular Biology, Inc., USA.

Kay McLellan et al, Therapeutic Botulinum Type A Toxin: Factors Affecting Potency, Toxicon, 1996, p. 975-985, vol. 34:9, Elsevier Science Ltd, Great Britain.

Letter dated Jul. 28, 2005 from Kilburn & Strode to European Patent Office regarding summons to attend Oral Proceedings dated Jan. 14, 2005.

Letter dated Aug. 10, 2005 from Hoffmann-Eitle to European Patent Office regarding Oral Proceedings scheduled for Oct. 20, 2005.

Letter dated Aug. 19, 2005 from Kilburn & Strode to European Patent Office regarding Rule 71A EPC Submission in preparation for Oral Proceedings scheduled for Oct. 20, 2005.

Appeal Brief dated Apr. 3, 2006 to Technical Board of Appeal for European Patent No. 99 94 5649.4.

Roche Lexikon Medizin 5. Augage (in German with English translation), Apr. 25, 2006.

Shone, et al. Monoclonal antibody-based immunoassay for type A: *Clostridium botulinum* toxin is comparible to the mouse bioassay. Appl. Environ. Microbiol. 1985; 50(1):63-67.

Eutick, Malvin L. Statutory Declaration dated Mar. 23, 2006 for Australian Patent Application No. 58214/99 in the name of Solstice Neurosciences, Inc., entitled "Stable liquid formulations of Botulinum Toxin" and in the matter of opposition thereto by Allergan, Inc.

Exhibit ME-1 (Resume of Malvin L. Eutick) referred to in the Statutory Declaration of Malvin L. Eutick dated Mar. 23, 2006.

Exhibit ME-2 (Facts arguments presented in support of the opposition against European patent No. 1 112 082) referred to in the Statutory Declaration of Malvin L. Eutick dated Mar. 23, 2006.

Exhibit ME-3 (Shone, et al. Monoclonal antibody-based immunoassay for type A *Clostridium botulinum* toxin is comparible to the mouse bioassay. Appl. Environ. Microbiol. 1985; 50(1):63-67.) referred to in the Statutory Declaration of Malvin L. Eutick dated Mar. 23, 2006.

Hallis, et al. Development of novel assays for botulinum type A and B neurotoxins based on their endopeptidase activities. J. Clin. Microbiol. 1996; 34(8):1934-1938.

Marshall, Philip Andrew. Statutory Declaration dated Mar. 8, 2006 for Australian Patent Application No. 58214/99 in the name of Solstice Neurosciences, Inc., entitled "Stable liquid formulations of Botulinum Toxin" and in the matter of opposition thereto by Allergan, Inc. (33 pages).

Marshall, Philip Andrew. Statutory Declaration dated Mar. 8, 2006 for Australian Patent Application No. 58214/99 in the name of Solstice Neurosciences, Inc., entitled "Stable liquid formulations of Botulinum Toxin" and in the matter of opposition thereto by Allergan, Inc. (8 pages).

Exhibit PM-1 (Resume of Philip Andrew Marshall) referred to in the Statutory Declaration of Philip Marshall dated Mar. 8, 2006.

Exhibit PM-2 (Modern Pharmaceutics by Banker, et al.) referred to in the Statutory Declaration of Philip Marshall dated Mar. 8, 2006.

Exhibit PM-3 (Stability of Protein Pharmaceuticals by Ahern, et al.) referred to in the Statutory Declaration of Philip Marshall dated Mar. 8, 2006.

Exhibit PM-4 (Hexsel, et al. Comment on Multicenter, double-blind study of the efficacy of injections with botulinum toxin type A reconstituted up to six consecutive weeks before application. Dermatol. Surg. 2004; 30(5):823.) referred to in the Statutory Declaration of Philip Marshall dated Mar. 8, 2006.

Exhibit PM-4 (Ma, et al. Efficacy of reconstituted and stored botulinum toxin type A: an electrophysiologic and visual study in the auricular muscle of the rabbit. Plast. Reconstr. Surg. 2003; 111(7):2419-26; discussion 2427-31 (Abstract)) referred to in the Statutory Declaration of Philip Marshall dated Mar. 8, 2006.

Exhibit PM-4 (Hexel, et al. Multicenter, double-blind study of the efficacy of injections with botulinum toxin type A reconstituted up to six consecutive weeks before application. Dermatol. Surg. 2003; 29(5):523-9; discussion 529 (Abstract)) referred to in the Statutory Declaration of Philip Marshall dated Mar. 8, 2006.

Exhibit PM-4 (Alam, et al. Pain associated with injection of botulinum A exotoxin reconstituted using isotonic sodium chloride with and without preservative: a double-blind, randomized controlled trial. Arch. Dermatol. 2002; 138(4):510-4 (Abstract)) referred to in the Statutory Declaration of Philip Marshall dated Mar. 8, 2006.

Exhibit PM-4 (Klein, A. W. Dilution and storage of botulinum toxin. Dermatol. Surg. 1998; 24(11):1179-80 (Abstract)) referred to in the Statutory Declaration of Philip Marshall dated Mar. 8, 2006.

Exhibit PM-4 (Sloop, et al. Reconstituted botulinum toxin type A does not lose potency in humans if it is refrozen or refrigerated for 2 weeks before use. Neurology. 1997; 48(1):249-53 (Abstract)) referred to in the Statutory Declaration of Philip Marshall dated Mar. 8, 2006.

Exhibit PM-4 (McLellan, et al. Therapeutic botulinum type A toxin: factors affecting potency. Toxicon. 1996; 34(9):975-85 (Abstract)) referred to in the Statutory Declaration of Philip Marshall dated Mar. 8, 2006.

Exhibit PM-4 (Gartlan, et al. Crystalline preparation of botulinum toxin type A (Botox): degradation in potency with storage. Otolaryngol. Head Neck Surg. 1993; 108(2):135-40 (Abstract)) referred to in the Statutory Declaration of Philip Marshall dated Mar. 8, 2006.

Exhibit PM-5 (Coffield, et al. The site and mechanism of action of botulinum neurotoxin. In: *Therapy With Botulinum Toxin*. Edited by J. Jankovic and M. Hallett. New York: Marcel Dekker. 1994; p. 3-13.) referred to in the Statutory Declaration of Philip Marshall dated Mar. 8, 2006.

Exhibit PM-5 (Dasgupta, B. R. Structures of Botulinum Neurotoxin, Its Functional Domains, and Perspectives on the Crystalline Type A Toxin. In: *Therapy With Botulinum Toxin*. Edited by J. Jankovic and M. Hallett. New York: Marcel Dekker. 1994; p. 15-39.) referred to in the Statutory Declaration of Philip Marshall dated Mar. 8, 2006.

Moyer, Elizabeth. Statutory Declaration dated Apr. 14, 2006 for Australian Patent Application No. 58214/99 in the name of Solstice Neurosciences, Inc., entitled "Stable liquid formulations of Botulinum Toxin" and in the matter of opposition thereto by Allergan, Inc.

Annexure EM-1 (Resume of Elizabeth D. Moyer) referred to in the Statutory Declaration of Elizabeth D. Moyer dated Apr. 14, 2006.

Annexure EM-2 (Facts arguments presented in support of the opposition against European patent No. 1 112 082) referred to in the Statutory Declaration of Elizabeth D. Moyer dated Apr. 14, 2006.

Annexure EM-3 (Shone, et al. Monoclonal antibody-based immunoassay for type A *Clostridium botulinum* toxin is comparable to the mouse bioassay. Appl. Environ. Microbiol. 1985; 50(1):63-67.) referred to in the Statutory Declaration of Elizabeth D. Moyer dated Apr. 14, 2006.

Annexure EM-4 (Goodnough, et al Stabilization of botulinum toxin type A during lyophilization. Appl. Environ. Microbiol. 1992; 58(10):3426-3428.) referred to in the Statutory Declaration of Elizabeth D. Moyer dated Apr. 14, 2006.

Annexure EM-5 (Hallis, et al. Development of novel assays for botulinum type A and B neurotoxins based on their endopeptidase activities. J. Clin. Microbiol. 1996; 34(8):1934-1938.) referred to in the Statutory Declaration of Elizabeth D. Moyer dated Apr. 14, 2006.

Goodnough, et al. Chapter 12—Recovery of Type A botulinal toxin following lyophilization. ACS Symposium Series (Formulation and Delivery of Proteins and Peptides). 1994; 567:193-203.

Sommer, et al. Botulinus toxin. J. Infectious Diseases. 1932; 51:243-253.

Woolford, et al. Heat inactivation of botulinum toxin Type A in some convenience foods after frozen storage. J. Food Science. 1978; 43:622-624.

Collin, P. H., et al. Saline. In Pons Fachworterbuch Medizin dictionary (p. 368).

Unseld, D. W. (1991). Saline. In Medical Dictionary of the English and German Languages (p. 280).

Urban & Schwarzenberg. Saline. In Roche Lexikon Medizin dictionary (p. 1400).

Walber de Gruyter. Saline. In Psychyrembel Klinisches Worterbuch dictionary (p. 1483).

Decision Revoking the European Patent No. 1112082 dated Nov. 22, 2005 from the European Patent Office.

M.C. Goodnough, et al. "Stabilization of Botulinum Toxin Type A during Lyphilization," Applied and Environental Microbiology, 58: 3426-3428 (1992).

P. Hambelton, et al. "Potency equivalence of botulinum toxin preparations", Journal of the Royal Society of Medicine 87: 719 (1994).

K. McClellan, et al. "Therapeutic Botulinum Type A Toxin: Factors Affecting Potency," Toxicon, 34(9): 975-85 (1996).

E.J. Schantz, et al. "Properties and Use of Botulinum Toxin and Other Microbial Neurotoxins in Medicine," Microbiological Reviews, 56(1): 80-99 (1992).

E.J. Schantz, et al. "Preparation and Characterization of Botulinum Toxin Type A for Human Treatment," in "Therapy with Botulinum Toxin," ed. J. Jankovic and M. Hallett, Marcel Dekker Inc. pp. 41-49 (1994).

J.P. Doweiko, et al. "Role of Albumin in Human Physiology and Pathophysiology," Journal of Parenteral and Enteral Nutrition, 15: 207-211 (1991).

B. Asher "Traitment des rides fronto-orbitaires par injections de toxine botulique, lifting endoscopique, et resurfacing laser," J. Med, Esth et Chir. Derm. XXIII:159-166 (1996) [*French language only*].

\* cited by examiner

STABLE LIQUID FORMULATIONS OF BOTULINUM TOXIN

This application claims the benefit of U.S. Provisional Application No. 60/099,870 filed Sep. 11, 1998, which is hereby incorporated herein by reference in its entirety.

FIELD OF THE INVENTION

The invention relates to therapeutic formulations of botulinum toxin that are stable to storage in liquid form at 0–10° C. for periods of at least one to two years.

REFERENCES

Consky, E. S., Lang, A. E. (1994) In: *Therapy with Botulinum Toxin.* Jankovic, J and Hallet M, eds. Marcel Dekker, Inc., New York.

Frankel, A. S., and Kamer, F. M. (1998) Chemical browlift. *Arch. Otolaryngol. Surg.* 124(3): 321–323.

Gartlan, M. G., and Hoffman, H. T. (1992) Crystalline preparation of botulinum toxin type A (Botox): Degradation in potency with storage. *Otolaryngology—Head and Neck Surgery* 102(2): 135–140.

Hambleton, P., Capel, B., Bailey, N., Heron, N. I., Crooks, Al, Melling, J. (1981) Production, purification and toxoiding of *Clostridium botulinum* type A toxin. *Biomedical Aspects of Botulism*, Academic Press, NY.

Hardman, J. G. and Limbird, L. E., Exec. Eds. (1996) Goodman & Gilman's *The Pharmacological Basis of Therapeutics*, 9$^{th}$ Ed. McGraw-Hill, New York.

Hoffman, H. T., and Gartlan, M. G. (1993) Stability of botulinum toxin in clinical use. *Botulinum and Tetanus Neurotoxins* (B. R. DasGupta, Ed.), Plenum Press, NY.

Johnson, E. A., Goodnough, M. C., Borodic, G. E., (1997) U.S. Pat. No. 5,696,077.

Lachman, L., Lieberman, H. A., Kanig, J. L. (1986) *The Theory and Practice of Industrial Pharmacy* (3$^{rd}$ Ed.), Lea & Febiger, Philadelphia Melling, J., Hambleton, P., and Shone, C. C. (1988) *Clostridium botulinum* toxins: nature and preparation for clinical use. *Eye* 2: 16–23.

*Physician's Desk Reference*, 51$^{st}$ Edition, 1997. ("PDR") Medical Economics Company, Inc, Montvale, N.J.

Schantz, D. J. and Kautter, D. A. (1978) Standardized assay for *clostridium botulinum* toxins, J. Assoc. Off. Anal. Chem 61:1.

Simpson, L. L. (1993) The actions of clostridial toxins on storage and release of neurotransmitters. *Natural and Synthetic Neurotoxins*, A. L. Harvey, Ed., Academic Press Ltd., San Diego, pp. 277–317.

Tsui, J. K. C. (1986), *Lancet* 2: 245–247.

BACKGROUND OF THE INVENTION

Botulinum toxin is a polypeptide product of the anaerobic bacterium *Clostridium botulinum*. The toxin causes muscle paralysis in mammals by blocking presynaptic release of the neurotransmitter acetylcholine at the neuromuscular junction. While the toxin has long been associated with fatal botulism, in recent years it has been used therapeutically to treat certain involuntary muscle movement disorders including focal dystonias (such as strabismus, essential blepharospasm and hemifacial spasm), as well as segmental dystonias (such as torticollis, oromandibular dystonia, and spasmodic dysphonia) and spasticity. The toxin has also found utility in various cosmetic indications, such as non-surgical reduction of "frown lines" on the face as well as in the treatment of hyperhydrosis (excessive perspiration).

Currently, there are two botulinum toxin (type A) preparations that are approved for therapeutic use in humans—"BOTOX®" (Oculinum®; Allergan Inc., Irvine, Calif.) and "DYSPORT®" (Spexwood Pharmaceuticals, Ltd.; U.K). Both these formulations are provided to clinicians in lyophilized (freeze-dried) form for reconstitution just prior to use.

Due to patient-to-patient variations in dosage requirements, the dosage needed for any individual patient may vary considerably. Moreover, for certain indications, the clinician must administer only a small fraction of the contents of a prepared vial over a protracted period of time, which may be several hours. Although one published study has indicated that liquid botulinum toxin formulations can be re-frozen and thawed with substantial retention of activity (Schantz and Kautter, 1978), more recent studies assessing the activity of the reconstituted toxin have demonstrated that "BOTOX®" loses at least 44% of its potency when it is reconstituted and stored under standard refrigerator (approximately 4° C.) for 12 hours. Moreover, when the reconstituted formulation was stored in a sub-zero freezer at −70° C., it lost about 70% of its potency after two weeks (Gartlan and Hoffman, 1993). For these reasons, it is recommended that such compositions not be used later than 4 hours after reconstitution. This can result in a significant waste of drug and cost to the patient.

There is therefore a need for a ready-to-use liquid formulation of botulinum toxin that can be conveniently shipped, stored and used as needed by the clinician. The present invention provides such a formulation.

SUMMARY OF THE INVENTION

The present invention is directed to stable liquid formulations of botulinum toxin for use in pharmaceutical preparations. The formulations of the present invention have the advantage that, unlike currently available formulations, they are stable in liquid form during storage for protracted periods of time (1 year or longer) at standard refrigerator temperatures (approximately 4±2° C., or about 2–8° C., or, more generally, ranging from about 0–10° C.). In a related aspect, the formulations are stable in liquid form during storage at "room temperature" (about 25°, or more generally in the range of 10–30°) for at least six months. Such formulations are particularly useful in conditions in which reduction or inhibition of cholinergic nerve input to a region, particularly a muscle or muscle group, gland or organ is ameliorative. Examples of such conditions are described herein.

In one aspect, the invention includes a stable liquid pharmaceutical formulation that includes isolated botulinum toxin and a buffer that is capable of providing a buffered pH range between about pH 5 and pH 6. According to this general embodiment, the toxin is mixed in a buffered liquid to form a liquid formulation which has a pH of between 5 and 6, particularly between about pH 5.4 and pH 5.8, and preferably about pH 5.5–5.6. The resulting formulation is stable for at least one year, and as long as at least two years, at temperature ranging from about 0–10° C., or for at least 6 months at higher temperatures, as described above. Generally, in accordance with the invention, any of the known botulinum toxin serotypes (e.g., serotypes A, B, $C_1$, $C_2$, D, E, F, or G) or other serotypes having equivalent biological activity may be incorporated into formulations of the invention. In preferred embodiments, the botulinum toxin used in the formulation is botulinum toxin serotype A or B, isolated from *Clostridium botulinum*.

In preferred embodiments, botulinum toxin Type B is present as a 700 kilodalton molecular weight complex in the formulation, at a concentration of about 100–20,000 U/ml, and particularly between about 1000–5000 U/ml. When Type A is used, it will generally be present at a concentration of about 20–2,000 U/ml, and particularly between about 100–1,000 U/ml. If combinations of different serotypes are used in the formulation, their useful dosage or concentration ranges can be determined in proportion to the dosages and concentrations exemplified herein, according to their respective biological activities.

Buffers that can be used in the formulation are physiological buffers that are considered safe for injection into mammalian tissue, particularly into humans. Representative buffers include, but are not limited to phosphate, phosphate-citrate, succinate, acetate, citrate, aconitate, malate, and carbonate based buffer systems. Preferably, the formulation will also include an excipient protein, such as human serum albumin or gelatin. It is appreciated that equivalents of the foregoing exemplary buffers and excipient proteins will be recognized and utilized by persons having skill in the art. The toxin formulation of the invention may be packaged in any of a variety of containers or vials known in the art, while retaining its potency.

In a related aspect, the invention includes a method of treating a patient in need of inhibition of cholinergic transmission, such cholinergic transmission to selected muscle or muscle group or to a specific gland region, such as sweat glands, or to a particular organ having cholinergic innervation.

Examples of therapeutic and cosmetic treatments that can be treated using the botulinum toxin formulation include, but are not limited to blepharospasm, strabismus, hemifacial spasm, otitis media, spastic colitis, anismus, urinary detrusor-sphincter dyssynergia, jaw-clenching, curvature of the spine, spasticity, such as spasticity due to one or more of the group consisting of stroke, spinal cord injury, closed head trauma, cerebral palsy, multiple sclerosis and Parkinson's disease, and dystonia (e.g., spasmodic torticollis (cervical dystonia), spasmodic dysphonia, limb dystonia, laryngeal dystonia, oromandibular (Meige's) dystonia). The formulation can also be administered to the perineum (perineal muscles) of a patient who is in the process of giving birth to a child to cause relaxation of such muscles. Exemplary cosmetic indications of the formulation include administration to muscles that produce wrinkles or furrowed brow. Other indications for the formulation include myofascial pain, headache associated with migraine, vascular disturbances, neuralgia, neuropathy, arthritis pain, back pain, hyperhydrosis, rhinnorhea, asthma, excessive salivation, and excessive stomach acid secretion.

Particularly specified routes of administration of formulations of the invention include intramuscular, subcutaneous or iontophoretic administration. For example, in studies carried out in support of the present invention, botulinum toxin Type B was found effective in controlling cervical dystonia when administered intramuscularly in a divided or single daily dosage of between 5000–10000 Units.

According to another related aspect, the invention includes methods of treating patients who have developed immunity or resistance to a specific botulinum serotype with a stable liquid formulation that includes another serotype. For example, a patient who is refractory to botulinum toxin serotype A can be treated with a stable liquid formulation containing any of botulinum serotypes B, $C_1$, $C_2$, D, E, F or G, or a patient who is refractory to botulinum toxin serotype B can be treated with a stable liquid formulation containing any of botulinum serotypes A, $C_1$, $C_2$, D, E, F and G, to provide renewed efficacy.

DETAILED DESCRIPTION OF THE INVENTION

The present invention is concerned with stable liquid pharmaceutical botulinum toxin formulations and uses thereof. Currently, while botulinum toxin preparations are commercially marketed for a variety of therapeutic and cosmetic applications, due to the lability of the active toxin ingredient in solution, formulations must be reconstituted from lyophilized ingredients which have stringent storage requirements. For example, "BOTOX®" is provided as a lyophilized powder, which must be shipped and stored in a freezer at or below −5° C. and reconstituted by addition of a measured amount of saline solution just prior to use. Following reconstitution, it is recommended that the formulation be administered to the patient within 4 hours, and that any reconstituted product be refrigerated during this time (PDR, 1997); freezing and thawing of the reconstituted product is not recommended (Hoffman, 1993).

The present invention provides a stable liquid formulation which contains botulinum toxin and which is stable as a liquid for at least one year at standard refrigerator temperatures and for at least six months at room temperature. This formulation is advantageous, because it does not require unusual storage or transport conditions and because it reduces the possibility of errors in dilution of the toxin which could result in overdose.

I. Definitions

As used herein, the term "stable" refers to retention of biological activity or potency by a biologically active substance, specifically botulinum toxin, over a defined or indefinite period of time.

The term "botulinum toxin" refers to a biologically active protein or protein complex, usually derived from the bacterium *Clostridium botulinum*. The term refers to any of at least eight known serologically distinct toxins (A, B, $C_1$, $C_2$, D, E, F and G), as well as any additional botulinum toxins having the same general ability to inhibit cholinergic neurotransmission, which form the active molecule. Optionally, the term also includes a carrier protein that is also derived from *C. botulinum* and which complexes with the active molecule, as described in Section IIA herein. Botulinum toxin serotypes are related pharmacologically, as discussed below, but are immunologically distinguishable. Generally, the active toxin molecule has a molecular size of between about 145 and 170 kilodaltons (kD). In the context of the present invention, it is understood that the toxin protein includes toxins and carrier proteins that are isolated from natural sources, as well as corresponding toxins and carrier proteins that are produced recombinantly according to methods known in the art. Moreover, the term "botulinum toxin" includes proteins having amino acid sequences that include conservative amino acid substitutions, including deletions, with respect to known botulinum toxin sequences, as described below.

"Biological activity" of botulinum toxin refers to its ability to block neurotransmission at synapses having acetylcholine receptors by blocking acetylcholine release from nerve endings. This term is used interchangeably herein with the terms "inhibition of cholinergic transmission," "inhibition of cholinergic input," "reduction of cholinergic input"

and declinations thereof. In vitro assays for assessing biological activity of the toxin include the mouse $LD_{50}$ assay, as described herein. A "unit" of activity in this assay is defined as the amount of toxin protein required to kill 50% of mice tested at that dosage. A functional definition of this term is provided in Example 2, herein.

Common amino acids are referred to by their one- or three-letter abbreviations herein: alanine (A, Ala), cysteine (C, Cys), aspartic acid (D, Asp), glutamic acid (E, Glu), phenylalanine (F, Phe), glycine (G, Gly), histidine (H, His), isoleucine (I, Ile), lysine (K, Lys), leucine (L, Leu), methionine (M, Met), asparagine (N, Asn), proline (P, Pro), glutamine (Q, Gln), arginine (R, Arg), serine (S, Ser), threonine (T, Thr), valine (V, Val), tryptophan (W, Trp), tyrosine (Y, Tyr).

The term "liquid pharmaceutical formulation" refers to a pharmaceutically active preparation of drug or biological which is capable of being stored in a liquid pharmaceutical excipient, such as buffered saline or a physiological buffer, for an extended period of time. The formulation may be a concentrated formulation which is diluted in a similar or different liquid prior to use.

The term "buffer" refers to a compound, usually a salt, which, when dissolved in an aqueous medium serves to maintain the free hydrogen ion concentration of the solution within a certain pH range, when hydrogen ions are added or removed from the solution. A salt or solution is said to have a "buffering capacity" or to "buffer" the solution over such a range, when it provides this function. Generally, a buffer will have adequate buffering capacity over a range that is within ±1 pH unit of its pK. A "physiological buffer" is a buffer that is non-toxic to mammals, particularly humans, when administered as part of a pharmaceutical preparation. Examples of relevant physiological buffers in the context of the present invention are provided herein.

A "pharmaceutically acceptable liquid" is a liquid which is considered to be safe for consumption by or injection into mammals, particularly humans.

The term "excipient protein," as used herein, refers to a protein that is added to a pharmaceutically active preparation, but which confers no additional significant biological activity to the preparation. Examples of excipient proteins include, but are not limited to serum albumins, particularly human serum albumin, and gelatin. Such proteins will preferably be relatively non-immunogenic to the mammalian species into which the pharmaceutical formulation is to be administered.

The term "comprising" as used in the context of the present invention, and particularly in the context of the claims, is intended to have the meaning of the term "including", "containing" or "characterized by." A composition or method which "comprises" elements A, B and C may include, in addition to A, B and C, other unrecited elements, such as X or Y.

The term "about" as used in the context of the present invention, and particularly in the context of the claims, means "approximately" or "nearly." In the context of numerical values, without committing to a strict numerical definition, the term may be construed to estimate a value that is ±10% of the value or range recited.

All other terms used herein should be construed to take on the usual definitions known to persons skilled in the art or which are cited in a standard medical or scientific dictionary.

II. Botulinum Toxin

As mentioned above, botulinum toxin is a polypeptide product produced by various strains of *Clostridium botulinum*. These strains produce at least eight known serologically distinct toxins (A, B, $C_1$, $C_2$, D, E, F and G). *C. barati* and *C. butyricum* each produce a single serotype that is similar to serotypes E and F, respectively (Simpson, 1993). Generally, the toxin molecule has a molecular size of between about 145 and 170 kilodaltons (kD). In some cases, the active toxin molecule consists of two disulfide-linked chains formed from a progenitor polypeptide. For example, botulinum toxin Type B is produced from a single precursor polypeptide of 150 kD, which is nicked to generate two disulfide-linked fragments—a heavy chain (H-chain) of 100 kD and a light chain (L-chain) of 50 kD for maximal activity. The naturally occurring toxin binds noncovalently to non-toxic carrier proteins also produced by *C. botulinum*. These carrier proteins bind to the toxin chains to form complexes having as large as 900 kD (Type A), and preferably about 700 kD for Type B. The carrier proteins co-purify with the toxin and optimally form part of the formulations described herein.

The various botulinum toxin serotypes exhibit different binding specificities in cells. For example, Type A and Type E toxins appear to bind to the same synaptosomal binding site, while Type B toxin binds to a distinct site and does not compete for binding at the Type A/E binding site (Melling, 1988). While not wishing to be bound by a particular theory or mechanism of action, it is believed that the H-chain of the toxin provides neuronal cell binding and cell penetration activities, while the L-chain acts to inhibit acetylcholine release at the synapse. Further, it is believed that botulinum toxin types A and B use slightly different mechanisms for effecting inhibition of acetylcholine release: type A cleaves Synapse Associated Protein-25 (SNAP-25) and type B cleaves Vesicle-Associated Membrane Protein (VAMP, or synaptobrevin), both of which proteins are components of synaptic vesicle release from synapses.

All *C. botulinum* toxin serotypes produce a common physiological result in mammals. They all inhibit or block cholinergic synapse activity, which results in partial or total muscle paralysis or blockade or inhibition of organ or glandular function, depending on the site of administration. Accordingly, the formulation of the present invention can be used with any of the botulinum toxin serotypes derived from *C. botulinum* which are characterized by the above-described biological activities. Amino acid sequences of most of the presently known serotypes are also known or can be determined by methods known in the art. It is understood that in the context of the present invention, a botulinum toxin formulation should further be construed to include a recombinantly engineered botulinum toxin that has conservative amino acid substitutions with respect to such known sequences. Generally such substitutions will be made from standard substitution classes of naturally occurring amino acids. For example, standard substitution classes may be the six classes based on common side chain properties and highest frequency of substitution in homologous proteins in nature, as determined, for example, by a standard frequency exchange matrix known in the art, such as the Dayhoff frequency exchange matrix. Under the Dayhoff matrix, for example, the classes are Class I: Cys; Class II: Ser, Thr, Pro, Hyp, Ala, and Gly, representing small aliphatic side chains and OH-group side chains; Class III: Asn, Asp, Glu, and Gln, representing neutral and negatively charged side chains capable of forming hydrogen bonds; Class IV: His, Arg, and Lys, representing basic polar side chains; Class V: Ile, Val, and Leu, representing branched aliphatic side chains, and Met; and Class VI: Phe, Tyr, and Trp, representing aromatic side chains. In addition, each group may include related amino acid analogs, such as ornithine, homoarginine, N-methyl lysine, dimethyl lysine, or trimethyl-lysine in class IV, and a halogenated tyrosine in Group VI. Further, the classes may include both L and D stereoisomers, although L-amino acids are preferred for substitutions. By way of example, substitution of an Asp for another class III residue such as Asn, Gln, or Glu, is a conservative substitution.

While botulinum toxin activity can be measured using electrophysiological assays such as are known in the art, activity is generally measured by injecting the toxin into small animals, such as mice, and determining the dose of toxin required to kill, on the average, 50% of animals tested. This dose is referred to as the "lethal dose-50" or $LD_{50}$ and is defined as a biological activity unit. Doses for therapeutic applications are, by convention, standardized to such units. As discussed in further detail in Section IIIB below, the various serotypes may have different human therapeutic potencies as measured by $LD_{50}$ units. Therapeutic dosages can be titrated from this information, according to methods known in the art.

III. Preparation of Botulinum Toxin

This section describes methods for preparing botulinum toxin to be used in the formulation in accordance with the present invention.

A. Purification of Botulinum Toxin from *C. botulinum*

This section provides general methods for preparing purified botulinum toxin from cultured *C. botulinum* as exemplified by botulinum toxin Type B. In addition to the methods specifically cited herein, alternative methods for preparing botulinum toxin types A and B, as well as the other known serotypes, are known in the art.

As mentioned above, the active ingredient in formulations of the present invention is a proteinaceous component of *C. botulinum* extracts known as botulinum toxin, the active component of which has a molecular weight of between about 145–170 kD and which is usually present in a native protein complex which has a much higher molecular weight. This section provides exemplary methods for purification of various botulinum toxins, focusing on botulinum toxin serotypes A and B. It is understood that the general scientific literature provides guidance for alternative methods of purifying the toxins, and that persons skilled in the art will be able to identify such methods and apply them to the particular toxin desired for use in formulations prepared in accordance with the present invention.

Generally, botulinum toxin Type B is isolated as a complex from high titer fermentations of *C. botulinum* cultures. Stock cultures can be obtained in the United States by institutions holding a license from the Center for Disease Control (CDC) and w elsewhere, according to the national regulations on distribution of the organism. For purification of botulinum toxin Type B, *C. botulinum* Okra or Bean B are appropriate starting materials. Frozen stock cultures are inoculated into test tubes containing culture medium such as thioglycollate medium or trypticase peptone medium, and cultures grown and processed according to the methods described below and detailed in U.S. Pat. No. 5,696,077, incorporated herein by reference, and as described below.

Briefly, cultures are expanded according to methods known in the art to produce sufficient amount of bacterial starting material to produce a desired yield of toxin. Generally, about 20 liters of bacterial culture will be required to produce 0.5 grams of toxin. The culture is brought to room temperature, and the pH of the culture is adjusted to pH 3.5 with sulfuric acid or another suitable acid. The resulting precipitate is allowed to settle, and the cleared supernatant is decanted. Calcium chloride is then added to the precipitate with stirring and the volume is increased with deionized water, such that the final concentration of $CaCl_2$ is about 150 mM. The pH is raised to near neutrality (pH 6.5) and the toxin solution is clarified by centrifugation. The toxin is reprecipitated by adjustment of the pH to 3.7. The resulting precipitate is allowed to settle, and the toxic precipitate is collected by centrifugation, then re-dissolved in buffer (pH 5.5) and exhaustively dialyzed overnight against the same buffer. The dialyzed toxin is centrifuged and the resulting supernatant chromatographed through an anion exchange column (DEAE). The unbound fraction is collected and tested for protein content. Toxin complexes are precipitated from this fraction by addition of ammonium sulfate to about 60% saturation. The pellet is dissolved in phosphate buffer and dialyzed against the same buffer (pH 7.9). This purified toxin preparation can be used to prepare the formulation.

Methods for preparing botulinum toxin type A are also well known in the art. For example, Hambleton, et al (1981) and Melling, et al (1988), both of which are incorporated herein by reference, describe the production and purification of botulinum toxin type from *Clostridium botulinum* type A NCTC 2916. Cultures of the bacteria are grown up from a verified seed stock and inoculated into a 30 liter fermenter operated under anaerobic conditions, according to standard conditions known in the art. Toxin yield is monitored continuously (for example by $LD_{50}$ determination), and when maximum yield is achieved (roughly $2 \times 10^6$ mouse $LD_{50}$/ml), the culture is acidified (adjusted with 3 N $H_2SO_4$ to pH 3.5, and the toxin is harvested by centrifugation. This precipitated crude toxin is re-dissolved and extracted with 0.2 M phosphate buffer (pH 6.0), followed by ribonuclease treatment (100 μg/ml at 34°) and precipitation using $NH_4SO_4$ (60% saturation at 25°). The precipitate is then resuspended and subjected to DEAE-Sephacel ion-exchange chromatography at pH 5.5 (following batch pre-adsorption). Fractions are monitored for activity, and active fractions are again precipitated using $NH_4SO_4$ (60% saturation at 25°). The precipitate can be stored and re-dissolved to make a formulation of the invention, as described below.

Formulations of the present invention preferably include the toxin binding complex, such as are prepared according to the methods described with respect to botulinum toxin Types A and B, above, or utilize equivalent forms of botulinum toxin types $C_1$, $C_2$, D, E, F, or G, prepared according to methods known in the art. The titer of the toxin is determined by serial dilution of reconstituted toxin binding complex into an excipient protein, such as human serum albumin, avoiding bubbles and violent agitation such as by vortex mixing. According to convention, titer is determined in a mouse lethality assay, such as the mouse $LD_{50}$ assay described in Example 2. A working stock is diluted, aliquoted and lyophilized for storage. This stock solution is tested in assays to determine protein concentration, $LD_{50}$, purity and pharmaceutical suitability according to methods well know in the art and exemplified in Example 2 herein.

IV. Stable Botulinum Toxin Formulations

It is the discovery of the present invention that botulinum toxin can be made and stored in a stable liquid formulation that retains its potency for an extended period of time, e.g., at least 1–2 years, at "refrigerator" temperatures (i.e., about 5±3° C., or more specifically, about 4±2° C., or more generally, 0–10° C.) or at least about 6 months at "room temperature" (i.e., about 25° C., or more generally 10–30° C.). Such a formulation can be conveniently dispensed to humans or other mammalian species as a pharmaceutical without further re-constitution by the physician. The formulation is characterized by a pH of between about pH 5 and 6, preferably about pH 5.5–5.6, as maintained by appropriate buffering conditions. The formulation may also include one or more excipient proteins.

Example 1 provides details for the preparation of a formulation of botulinum toxin (type B) at a concentration of 5000 U/ml. It is understood that such formulation conditions may be applied to other serotypes of botulinum toxin such as botulinum toxin Type A, at the concentrations required for such serotypes, in order to provide stable formulations in convenient dosing packages.

Briefly, a concentrated preparation of botulinum toxin, such as the purified toxin preparations described above with reference to types A or B, is admixed with a diluent, such as succinate buffer having a pH between pH 5 and pH 6, preferably about pH 5.6. In the case of botulinum toxin Type B, a concentration of about 5000 U/ml, as assessed in the mouse $LD_{50}$ assay, is desirable; however anywhere in the range of 100–20,000 U/ml or even higher, may be needed or desirable, depending on the dosage to be delivered. In the case of botulinum toxin Type A, concentrations ranging from 20–2,000, and preferably about 100–1,000 U/ml may be convenient. For pharmaceutical manufacturing purposes, the formulation is sampled and tested for the presence of possible microbial contaminants (bioburden) and is sterile filtered into glass or polypropylene vials for dispensing to patients. The final product can be stored as a liquid for at least one year and preferably more than two years at 0–10° C. without significant loss of biological potency, as evidenced by <20% loss of potency in the mouse $LD_{50}$ test (Example 2).

The diluent referred to above can be any pharmaceutically acceptable liquid which will not adversely affect the stability of the complex, and which supports a stable pH range between about pH 5 and pH 6. Examples of particularly suitable buffers include succinate and phosphate buffers; however, those of skill in the art will recognize that formulations of the invention will not be limited to a particular buffer, so long as the buffer provides an acceptable degree of pH stability, or "buffer capacity" in the range indicated. Generally, a buffer has an adequate buffer capacity within about 1 pH unit of its pK. (Lachman, et al., 1986). In the context of the present invention, this includes buffers having pK's in the range of about 4.5–6.5. Buffer suitability can be estimated based on published pK tabulations or can be determined empirically by methods well known in the art. In addition to the succinate and phosphate buffers mentioned above, other pharmaceutically useful buffers include acetate, citrate, aconitate, malate, and carbonate (Lachman). The pH of the solution can be adjusted to the desired endpoint within the range using any pharmaceutically acceptable acid, for example hydrochloric acid or sulfuric acid, or base, for example sodium hydroxide.

The excipient protein added to the formulation can be any of a number of pharmaceutically acceptable proteins or peptides. Preferably, the excipient protein is selected for its ability to be administered to a mammalian subject without provoking an immune response. For example, human serum albumin is well-suited for use in pharmaceutical formulations that are administered to humans; conversely, bovine serum albumin might be selected for use in cattle. Other known pharmaceutical protein excipients, such as, for example gelatin, may be used for this purpose. The excipient is included in the formulation at a sufficient concentration to prevent adsorption of the toxin protein complex to the holding vessel or vial. The concentration of excipient will vary according to the nature of the excipient and the concentration of toxin complex in the formulation. By way of example, in studies carried out in support of the present invention, it has been determined that a concentration of 0.5 mg/mL human serum albumin is sufficient for purposes of formulations containing 5000 U/mL botulinum toxin Type B, while not evoking a significant immunological or allergic reaction in most humans; generally concentrations of between about 0.05 mg and 1 mg per 1000 U botulinum B should provide sufficient protection.

Appropriate excipient concentrations for stabilizing botulinum toxin type A have also been described. For example, "BOTOX®" is stabilized by addition of 0.5 mg albumin per 100 units of toxin activity (PDR).

V. Utility

A. Therapeutic and Cosmetic uses of Botulinum Toxin Formulations

The pharmaceutical compositions of the present invention can be used for a number of indications in which inhibition or blockade of cholinergic neurotransmission is desirable, particularly, but not limited to, cholinergic transmission associated with control of smooth or skeletal muscles. This section provides examples of disorders in which formulations of the invention can be used therapeutically; however, the examples provided herein should not be construed to limit the invention. Representative dosages and routes of administration for some of these indications are described in Part B, below.

Botulinum toxin, particularly botulinum toxin Type A, has been shown to be an effective treatment of spastic muscle disorders. A single treatment regimen (which may include multiple intramuscular injections) can provide relief from uncontrollable muscle spasm for as long as several months. For example, "BOTOX®" (botulinum toxin Type A) is approved by the U.S. Food and Drug Administration for localized injection into the ocular orbit for treatment of blepharospasm. Other indications include other focal dystonias, such as laryngeal dystonia, Meige's syndrome (oromandibular dystonia; orofacial dyskinesia), spasmodic torticollis (Hardman, et al., 1996), limb dystonia, animus, and urinary detrusor-sphincter dyssynergia, blepharospasm, strabismus, hemifacial spasm as well as rhinorrhea, otitis media, excessive salivation, asthma, spastic colitis, excessive stomach acid secretion (see, for example, U.S. Pat. No. 5,766,005), headache associated with migraine, vascular disturbances, neuralgia or neuropathy (U.S. Pat. No. 5,714,468; WO 953041), arthritis pain (WO 9517904), disorders of the gastrointestinal tract involving striated or smooth muscle (U.S. Pat. No. 5,674,205), relaxation of the perineum during childbirth (U.S. Pat. No. 5,562,899), or relief of jaw-clenching (U.S. Pat. No. 5,298,019). Botulinum toxin Type A has been also injected locally to achieve cosmetic relief of muscle tone which causes "frown lines" on the face and to achieve a "browlift" (Frankel, 1998) and has been found to be useful when injected intracutaneously for treating focal hyperhydrosis (excessive sweating; WO 9528171; U.S. Pat. No. 5,766,605) as well as for treating juvenile curvature of the spine (U.S. Pat. No. 5,053,005) adult and juvenile cerebral palsy (U.S. Pat. No. 5,298,019; WO 9305800), and spasms and involuntary contractions caused by cerebral palsy, multiple sclerosis or Parkinson's disease (U.S. Pat. No. 5,183,462). All references cited above are herein incorporated by reference in their entireties.

In experiments carried out in support of the present invention, stable liquid formulations containing botulinum toxin Type B have been tested and found efficacious in cervical dystonia, also known as torticollis, a condition in which an individual experiences involuntary spasms and muscle contractions in the head, neck and spine which result in turning or tilting movements of the head. This condition is also frequently accompanied by tremor and musculoskeletal pain. In general, the etiology of the disorder is unknown; however, it is considered to be the result of central nervous system dysfunction resulting in hyperactivity of the involved musculature. Current treatment regimens, including anticholinergic, dopaminergic, muscle relaxant, antispasmodic and anticonvulsant drugs, do not provide sustained relief. Botulinum toxin Type B is effective in treating this condition by causing local paralysis or paresis, which has a typical onset time of about 1 week after injection and duration of response lasting from about 1 to 4 months.

Formulations of the other botulinum toxin serotypes are useful in primary treatment of any of the conditions previously described with respect to Type A. In addition, as mentioned above, botulinum toxin Types B–G are also useful in treatment of patients who have become refractory to treatment with botulinum toxin Type A due to the presence of an immune response to the toxin. Conversely, serotype A may be used in patients who become refractory to serotype B or any of the other toxin serotypes. Formulations of one or more botulinum toxin serotypes can be made and used in accordance with the present invention.

Generally, it is appreciated that, in view of their similar biological effects, the various botulinum toxin types may be interchangeable in the treatment of various disorders, particularly those related to muscle spasticity. Nonetheless, as described below with respect to types A and B, effective dosages (expressed in terms of $LD_{50}$'s or biological units) may vary significantly among the various serotypes. Estimates of equivalent dosages can be made based on the known dosages described with respect to any of the tested toxins.

B. Dosages and Modes of Administration

Botulinum toxin is known as a potent and sometimes fatal toxin to animals. Nonetheless, as described below, when sufficient care is taken in adjusting the mode of administration and dosage, this drug can be used safely in humans.

Dosages for the various forms of botulinum toxin will vary, according to the serotype of toxin used. For example, in experiments carried out in support of the present invention it has been found that, comparing mouse $LD_{50}$ units, botulinum toxin Type A ("BOTOX®") is about 4–6 times more potent than botulinum toxin Type B in inducing paralysis in monkeys, as assessed by electrophysiological measurements of selected skeletal muscles. This observation is consistent with experimental results in rats that showed large differences in the amounts of the two toxins required to produce paralysis of rat limbs (Sellin; Jackson). In view of these observations, appropriate equivalent dosages can be estimated or determined empirically by the skilled practitioner.

Variation in the recommended dosage may also vary in accordance with patient history. Patients who have received repeated doses of botulinum toxin type A, for example, have been reported to become "resistant" to further treatment, requiring larger doses to produce an equivalent effect over time. Without committing to any particular mechanism of action, it is believed that this phenomenon is related to development in the patient of a serotype-specific immune response. Reports on the incidence of antibodies in patients undergoing repeated botulinum toxin Type A therapy range from about 3% to 57%. Accordingly, it is recommended that in the event that the clinician elects to switch serotypes during a treatment regimen, the initial dosage of the new serotype should be calculated on the basis of a naïve patient, rather than on the basis of the patient's dosage history.

Appropriate methods of administration include any which will result in delivery of the active toxin ingredient to the tissue of interest, without causing severe side effects to the patient. Such methods include, without limitation, intramuscular (i.m.) injection, topical administration, subdermal, perineural application, iontophoretic current administration, and the like. Specific procedures for administration of botulinum toxins, including maneuvers to limit systemic distribution of active components, are well known in the art. Electromyography may be used to identify and more precisely locate specific muscle groups, particularly for treatments involving muscles that are difficult to identify, such as those in the orbit of the eye, the larynx and the pterygoid area, as well as muscles in obese subjects.

Treatment of dystonias usually is accomplished by administering the toxin into the vicinity of the zones of innervation of the affected muscle, usually by intramuscular injection using a hypodermic needle. Typically, the resulting localized paralysis can provide relief to a patient for up to 3 or 4 months. Patients may be tested at lower doses and individually titered up to an optimal dose, in order to achieve sufficient neuromuscular blockade to correct any dysfunction without producing frank paralysis. Changes in dosage may be indicated if the patient becomes resistant to toxin. An advantage of the present invention is that it overcomes a common dosage problem related to instability of the toxin material in solution, which can lead to further ambiguities concerning appropriate dosage.

Recommended dosages of botulinum toxin Type A have been determined for a number of indications and are known in the art. For example, for treatment of strabismus, a dosage of 1.25–2.5 U botulinum toxin type A is recommended for administration to vertical muscles and for horizontal strabismus of less than 20 diopters; 2.5–5 U is recommended for horizontal strabismus of greater than 20 prism diopters (*Physician's Desk Reference*, 51$^{st}$ Edition).

Botulinum toxin Type A is also used for treatment of blepharospasm at a dosage of 1.25–2.5 U injected, using a 27–30 gauge needle, into the medial and lateral pre-tarsal orbicularis oculi of the upper lid and into the lateral pre-tarsal orbicularis oculi of the lower lid. Treatments are expected to last about 3 months; at repeat treatment, the dosage may be increased up to two-fold, depending on the response of the patient. It is recommended that a cumulative dose of no more than 200 U botulinum toxin type A should be given over a 30 day period (*Physician's Desk Reference*, 51$^{st}$ Edition).

Example 3 provides examples of dose ranging studies for use of botulinum toxin Type B in the treatment of cervical dystonia (torticollis) using a formulation in accordance with the present invention. In these studies, also outlined below, botulinum toxin Type B liquid formulation in accordance with the invention was provided to the administering clinicians with instructions to store the formulation in a clinical refrigerator with control for temperatures between 2–8° C. Generally formulation was supplied from lots prepared and stored at the recommended temperature for 6–12 months. Clinicians received an approximate 6 month supply of the formulation.

Briefly, patients were given variable doses of toxin, by intramuscular (i.m.) injection into 2–4 superficial neck and/or shoulder muscle groups, determined in accordance with the clinicians evaluation of muscle involvement in the disorder. In one study, individual divided doses ranging from 100–1200 U were given, with cumulative doses of between 270–2280 U over a period ranging up to 398 days. All patients experienced improvement during the study and no diminution of formulation potency was observed in the course of the study.

Further studies carried out in support of the present invention revealed that patients who have become resistant to botulinum toxin type A can be treated with botulinum toxin Type B. Here patients who participated in the study exhibited a decreased responsiveness to botulinum toxin type A and were considered successfully treated if, after treatment, they exhibited at least a 25% decline in Total score (decline=improvement) as assessed by the Toronto Western Spasmodic Torticollis Rating Scale (TWSTRS; Consky, 1994), in comparison to baseline score. Individual doses between 150–1430 U of botulinum toxin Type B formulation were administered, with cumulative doses ranging from 300–12000 units over up to 117 days as detailed in Example 3. Overall, patients experienced an improvement in this study, particularly at higher doses, and there was no evidence of development of blocking antibodies to botulinum type B, nor was there evidence of diminution of potency of the formulation. In a further study, individual doses of 0, 400, 1200, and 2400 U botulinum toxin Type B formulation were administered periodically for periods as long as 203 days, with success in treating torticollis, as described above.

The following examples illustrate, but in no way are intended to limit the present invention.

EXAMPLES

Materials

Unless otherwise indicated, all reagents described herein can obtained from any reputable commercial vendor that sells reagents for use in the chemical, biochemical, biotechnological or pharmaceutical industries, as appropriate.

Example 1

Preparation of Stable Botulinum Toxin Formulation

A. Preparation of Succinate Buffer

Succinate buffer was prepared in 3 L lots with 2.7 mg/mL disodium succinate and 5.8 mg/mL sodium chloride, supplemented with 0.5 mg/mL human serum albumin (Michigan Biological Products Institute). Concentrated hydrochloric acid was used to adjust the pH of the buffer to pH 5.6. The buffer was filtered through a 0.21 µm filter into an autoclaved, sealed container. Prior to use, the buffer was sampled and tested for pH, bacterial endotoxin and bioburden.

B. Preparation of Botulinum Toxin Formulation

An aliquot of concentrated botulinum toxin Type B was diluted approximately 1000-fold using succinate buffer (pH 5.6) to obtain a potency of 5000±1000 U/ml. The diluted toxin was stored in 2 L sealed glass containers and is referred to as "Bulk Solution." It was then stored at 5±3° C. until the material was shipped for filling.

Prior to filling, the Bulk Solution was sampled and tested for the presence of microbial contamination (bioburden) according to standard methods known in the art. It was then transferred by peristaltic pump via medical grade tubing, and sterile filtered (0.2 µm) into a sterile bulk receiver located inside the filling room. The resulting sterile filtered Bulk Solution was filled into 3.5 cc glass vials in aliquots of 0.5 mL (2500 U), 1 mL (5000 U) or 2 mL (10000 U).

The composition of the final container product is shown in Table 1.

TABLE 1

Composition of Botulinum B Formulation

| Active Ingredient | Inactive Ingredients | Concentration |
|---|---|---|
| Botulinum toxin Type B | — | 5000 ± 1000 $LD_{50}$ U/mL |
| — | Succinate, USP | 10 mM |
| — | Sodium chloride, USP | 100 mM |
| — | Human albumin, FDA released | 0.5 mg/mL |
| — | Hydrochloric acid, NF | For pH adjustment |

Example 2

Stability Testing of Botulinum Toxin Formulation

A. Stability Results

Botulinum toxin Type B was manufactured, diluted as described above to a concentration of 2500 Units/ml, and stored as 1 mL aliquots in 5 mL glass vials at 5° C. for up to and including 30 months. At 0, 1, 3, 6, 9, 12, 18, 24 and 30 months following initial storage, aliquots were chosen at random and tested for potency in the mouse $LD_{50}$ assay. The solutions were also observed for appearance and were tested for pH according to standard methods.

Table 2 shows the results of testing of aliquots removed at various timepoints. These results indicate that formulations prepared in accordance with the present invention are stable, as evidenced by a potency that is within the range of potencies reported at time zero, for at least 30 months when stored at 5° C.

TABLE 2

Stability of Formulation at 5° C.

| Storage time (months) | Potency (mean; U/ml) | pH | Appearance[a] |
|---|---|---|---|
| 0 | 1750–3250 | 5.5 | Pass |
| 1 | 1941 | ND[b] | ND |
| 3 | 2541 | 5.6 | ND |
| 6 | 2020 | 5.6 | Pass |
| 9 | 2357 | 5.6 | Pass |
| 12 | 2064 | 5.6 | Pass |
| 18 | 2318 | 5.4 | Pass |
| 24 | 1799 | 5.6 | Pass |
| 30 | 2101 | 5.6 | Pass |

[a]Pass = clear, colorless to light yellow solution; substantially free of visible particles
[b]Test not performed Table 3 shows the results of testing on aliquots of botulinum type B toxin formulation prepared and aliquoted as described above, but stored at 25° C. These results indicate that the formulation is stable for at least 6 months at 25° C., as evidenced by a mean potency that retains at least about 90%, and preferably at least 95%, after 6 months storage, and at least about 75% of its initial potency after 9 months storage at 25° C.

TABLE 3

Stability of Formulation at 25° C.

| Storage time (months) | Potency (mean; U/ml) | pH | Appearance[a] |
|---|---|---|---|
| 0 | 1941 | 5.5 | Pass |
| 1 | 2297 | 5.6 | ND[b] |
| 2 | 1935 | 5.6 | ND |
| 3 | 2017 | 5.6 | ND |
| 6 | 1909 | ND | Pass |
| 9 | 1579 | 5.6 | Pass |

[a]Pass = clear, colorless to light yellow solution; substantially free of visible particles
[b]Test not performed

B. Stability Tests

1. Determination of pH of Botulinum Toxin Formulation

The pH of the botulinum toxin Type B formulation was measured using a Fisher Scientific Accumet pH Meter, Model 50 with an automatic temperature compensation probe. The electrode was an Orion Ross Combination Electrode with a KCl reference electrode. The pH determination was made following a standard two-point standardization (pH 4.0, pH 7.0) according to manufacturer's directions. Three measurements are made for each sample. The pH values were recorded to 2 significant figures and the average was taken.

2. Mouse $LD_{50}$ Potency Test

Healthy, unused CFW or CD-1 mice of either sex weighing 18 to 22 g were used to determine $LD_{50}$. For each filled product, mice were tested at 5 doses of botulinum toxin Type B formulation. Each assay was run in quintuplicate.

Two stock solutions were prepared from the test sample. Stock Solution A was obtained by diluting the test sample to an estimated potency of 750 U/mL with gelatin phosphate buffer, pH 6.2. Stock Solution B was obtained by diluting solution A 10-fold to 75 U/mL. The following test dilutions were prepared from Stock solution B: 1:7.5, 1:10, 1:13.5, 1:18, and 1:24.3.

Mice were given intraperitoneal injections of 0.2 mL of the appropriate dilution of compound. The mice were held for 4 days post-injection and observed daily. Any deaths were recorded. The observations were terminated after four days.

Cumulative Deaths (CD) at the different dilution levels were calculated by adding the number of deaths from the maximum dilution upwards. The Cumulative Survivors (CS) were calculated by adding the number of survivors from the minimum dilution downwards. The % CD was calculated as CD/(CD+CS)×100% at each dilution. The dilution representing the $LD_{50}$ was determined by the Proportional Distance (PD) method of Reed and Muench using the dilutions producing % CD values that bracket the 50% Cumulative Death.

$$\text{The Proportional Distance } (PD) = \frac{(\%CD > 50\%) - 50\%}{(\%CD > 50\%) - (\%CD < 50\%)}$$

The PD value obtained was multiplied by the log difference between the dilution levels which bracket the 50% CD. This value was added to the log of the dilution with mortality (CD) greater than 50 to obtain the dilution representing the $LD_{50}$. The antilog of this dilution was calculated to obtain the number of $LD_{50}$ units of toxin per injection volume (0.2 mL). This number was then multiplied by 5 to obtain the $LD_{50}$ units per mL of toxin Stock Solution B.

The $LD_{50}$ units per mL of Stock Solution B were multiplied by its dilution factor (i.e. the dilution required to produce an estimated potency of 75 U/mL) to obtain the potency of the sample. The arithmetic mean and standard deviation of $LD_{50}$ units per mL were calculated for 5 valid tests.

3. Appearance of Formulation

Appearance was assessed through visual inspection against black and white backgrounds under bright light following a gentle swirl. The color, clarity and presence of visible particulates were all evaluated.

Example 3

Treatment of Cervical Dystonia (CD)

A. Drug Dilution, Calculation, Administration and Dosing Regimen

1. Drug Handling

Vials of drug were filled to deliver 2.0 mL (10000 U), 1.0 mL (5000 U) or 0.5 mL (2500 U) of undiluted study drug. Violent agitation or bubbling were avoided in all handling steps, since botulinum toxin can be denatured by either of these conditions. The formulation was removed from the vial using a 1 mL tuberculin syringe, ensuring that the exact volume was removed.

2. Drug Calculation

Botulinum toxin Type B was administered to cervical dystonia (CD) patients by administering the contents of the appropriate vial(s) to provide the dosages indicated in the table below. The mouse units (U) for dose escalation is calculated as follows, where 1U is the amount of toxin present in a dose which represents the $LD_{50}$, determined in mice as described in Example 2.

For each dosing session, botulinum toxin Type B was administered according to standard procedures, as detailed below. Injections of compound were given by a neurologist physician previously trained in the therapeutic use of botulinum toxin in patients with CD. Patients were requested to relax as much as possible to facilitate observation of the head and neck posture at rest. Determination of the neck muscles involved in producing the CD was made and confirmed by palpation of the involved muscles. At the discretion of the Investigator, EMG evaluation was performed to further locate the primarily affected muscles. The muscles considered for treatment in this protocol are levator scapulae, scalenus medius and anterior, semispinalis capitism, splenius capitus, sternocleidomastoid, and trapezium. Injections were made into each of these muscles in 1 to 5 sites. Total injection volume per site was less than or equal to 1.0 mL to avoid local tissue distortion, but at least 0.1 mL to facilitate accurate volume measurement with a standard 1.0 mL syringe. Initially, patients received a total dose of 5000 U, with subsequent doses of up to about 15000 units on follow-up visits to the clinic.

B. Clinical Studies of Cervical Dystonia (CD)

Study 1

Eight patients (3 males, 5 females) having a mean age of 43.9 years and individual clinical diagnoses of idiopathic CD took part in a study in which botulinum toxin Type B formulation was injected into 2–4 superficial neck and/or shoulder muscle groups. Patients were allowed to undergo treatment as frequently as every 4 weeks, provided there were no serious adverse effects or persistent clinical improvement at presentation. Patients participated in 1–5 dosing sessions. Individual dosing sessions ranged from 100 U to 1200 U with total cumulative doses ranging from 270 U to 2280 U botulinum toxin by Type B toxin formulation as described herein. Effectiveness was assessed by use of the Tsui Torticollis Scale (Tsui, J. K. C. (1986), *Lancet* 2: 245–247). Patients participated in the study for 127 to 398 days, with a mean time in study of 244.8 days. Torticollis scores were similar at baseline, and all patients experienced a modest decline in score (decline improvement) with some indication of a dose-related trend, when total dosages were compared. Overall, patients experienced an improvement in torticollis conditions. There was no indication of development of blocking antibodies in this study.

2. Study 2

Patients enrolled in this study had a clinical diagnosis of idiopathic CD (torticollis) and had developed resistance to botulinum toxin type A. Patients received intramuscular injections of botulinum toxin Type B formulation in accordance with the present invention to 2–4 superficial neck and shoulder muscles.

Twelve patients (median age 52.3 years) entered and completed the study. Patients participated in the study from 37 to 127 days, with a mean time of 65 days. Patients were treated with 1 to 3 doses of study drug. Cumulative doses ranged from 940–2100 U, and individual doses ranged from 150–1430 U of botulinum toxin Type B. The mean length of time between dosing sessions was 22.3 days for patients receiving lower doses (100–899 U total) and 48.4 days for those in the higher dose range (900–1500 U).

Clinical benefit was defined as at least a 25% decline in score in the Toronto Western Spasmodic Torticollis Rating Scale (TWSTRS)—Severity Scale (Consky, E. S., Lang, A. E. (1994) In: *Therapy with Botulinum Toxin*. Jankovic, J and Hallet M, eds. Marcel Dekker, Inc., New York) as compared to baseline (decline=improvement). The mean score was similar in all patients at baseline. 56% of patients in the higher dose group exhibited a decline in TWSTRS-severity score, as compared to 7% of patients in the lower dose group. A modest improvement in TWSTRS—pain scores was also observed in both groups, particularly in the early phases of the study. There was no evidence of development of blocking antibodies to botulinum toxin Type B in these patients.

3. Study 3

Twenty-eight patients (mean age 50.9 years) with a confirmed diagnosis of cervical dystonia received injections of botulinum toxin Type B formulation into 2–4 superficial neck and shoulder muscles with escalating doses (up to 1.5-fold per successive session) over time. Clinical benefit was assessed using the TWSTRS-Severity test, as described above, with a 25% reduction in score considered an improvement.

Patients participated in the study from 28–177 days with a mean time in the study of 71.9 days. Patients were treated with 1 to 3 doses of formulation. Cumulative doses ranged from 1430 U to 12000U, with individual doses ranging from 300 U to 12000 U. For purposes of clinical assessment, 4 dose groups were defined: 100–800 U (Group A), 900–2399 U (Group B), 2400–5999 U (Group C), and 6000–12000 U (Group D). The length of time between dosing sessions ranged as follows: Group A, 13–101 days, avg. 35.7 days; Group B, 14–113 days, avg. 48.8 days; Group C, 29–177 days, avg. 62.2 days; Group D, 28–177 days, avg. 55.1 days.

Mean baseline scores were similar in all patients in all treatment groups, and all 4 groups experienced a mean decrease in score (improvement) during the study. Overall, mean percent improvement from baseline and mean response ratio for severity score was greatest in Groups C and D during the study. Measures of mean maximum improvement, mean maximum percent improvement and mean maximum response ratio were greater for the two higher dose groups than for the two lower dose groups (8.1 and 6.8 vs. 2.1 and 3.6 for maximum improvement; 43.9% and 35.5% vs. 10% and 16.1% for mean maximum improvement; 0.32 and 0.23 vs. 0.05 and 0.09 for mean maximum response ratio). The percentage of patients responding to treatment was greater for the two higher dose groups (C, 80% and D, 78%) than for the two lower dose groups (A, 0% and B, 27%). The mean duration of response was longer for the two higher dose groups (C, 47.6 days; D, 38.1 days) than for the two lower dose groups (A, 0 days; B, 31 days). These data show a dose-dependent response to botulinum b toxin formulations in accordance with the present invention.

4. Study 4

Three doses of botulinum toxin Type B formulation were tested against placebo treatment in a study which included 85 CD patients entering a randomized, double-blind, single-dose, 4-arm, parallel-group, multi-center study. Patients ranged in age from 18 to 80 years. Doses were 400, 1200 or 2400 U botulinum toxin Type B injected into 2–4 superficial neck and/or shoulder muscle groups. Patients were assessed using the TWSTRS scoring scale at baseline and at weeks 2 and 4 after treatment. Patients who failed to show 3 or more points improvement ($\geq$20%) in TWSTRS severity score after 4 weeks were withdrawn from the study as non-responders. Responders returned for assessment every 4 weeks, until their response levels fell by greater than 50%.

All TWSTRS scores showed improvement with increasing dose of botulinum toxin Type B formulation. At week 4, there was a statistically significant improvement in patients in the 2400 U dose group as compared to placebo-treated patients by both the TWSTRS-pain and TWSTRS-total assessments, and the percentage of patients showing improvement was greatest in the 2400 U group. Mean patient global assessments were considerably higher in the 2400 U group at weeks 2, 4 and 8 as compared to any of the other treatment group; in analyses of variance on the week 4 data, there was a statistically significant difference (p=0.0286) among treatment groups. There were also significant differences between placebo and the 2400 U dose group (p=0.0050) and in the dose-response analysis (p=0.0028). In the analyses of variance of Week 4 data, there was a statistically significant difference (p=0.0073) among the treatment groups, and there were also significant differences between placebo and the 2400 U dose group (p=0.0015) and in the dose-response analysis (p=0.0008).

Patients participated in this study from 25 to 203 days, with a higher average number of days for the 2400 U dose group (61 days).

5. Study 5

This study was also a randomized, double-blind, placebo-controlled, single dose, 4-arm, parallel group, multi-center outpatient study examining the effects of a single treatment of placebo (Group A) or one of three doses (2500 U, Group B; 5000 U, Group C; 10000 U, Group D) of botulinum toxin Type B formulation injected into 2 to 4 superficial neck and/or shoulder muscle groups in patients with confirmed diagnosis of CD. Patients ere evaluated at visits 2 and 4 weeks after treatment. Those with greater than 20% improvement at week 4 compared to baseline (TWSTRS-total score) were considered "responders" and were asked to return for re-evaluation at 4 week intervals for a maximum of 4 months, or until their response score level fell by greater than 50%.

One hundred twenty-two patients, ranging in age from 19–81 years, entered the study. The time the patients continued in the study reflected the time that they responded to study drug. Treatment groups were similar for the minimum and maximum number of days that patient members remained in the study. The mean time in the study increased as the dose increased, from 45 days for placebo Group A, to 61 days (B), 67 days (C) and 75 days (D).

For all TWSTRS scores, all treatment groups showed improvement from baseline to week 4. All of the TWSTRS scores tended to improve as the dose of formulation increased. In the analysis of covariance on the Week 4 TWSTRS-total scores, the overall difference among treatment groups was statistically significant (p=0.0001). In addition analysis of dose-response was significant (p=0.0001), and all 3 comparisons of placebo with the active groups were significant (p=0.0016 for placebo vs 2500 U; p=0.0005 for placebo vs 5000U; p=0.0001 for placebo vs 10,000 U). The percentage of patients who responded to treatment at Week 4 was greater in Group D (10000 U) than in any other group for TWSTRS-total, -disability, and -pain scores. There was a significant dose-response for each of the four TWSTRS scores (total, p<0.001; severity, p=0.035; disability, p=0.002; pain, p=0.001). Pain assessment improved for all treatment groups at Week 4, to 67.5, 70.2 and 75.1 in groups B, C, and D, respectively. Overall differences among treatment groups was statistically significant (p=0.0049), the analysis of dose-response was statistically significant (p=0.0017) and the comparisons of placebo with all three active treatment groups were significant (p=0.0149, 0.0084 and 0.0007 for groups B, C and D, compared with placebo, respectively).

Example 4

Physiological Response to Botulinum Toxin Type B formulation in Human Subjects

Eighteen healthy subjects were tested for extensor digitalis brevis (EDB) M-wave amplitude response to botulinum toxin Type B using standard electrophysiological methods known in the art. Subjects ranged in age from 18–22 years. Electrophysiological studies were carried out on days 2, 4, 6, 9, 11, 13 and 14 post-injection of doses ranging from 1.25 U to 480 U (i.m.) of botulinum toxin Type B formulation. The results of analysis of the data showed a dose-dependent decrease in EDB M-wave amplitude and area with increasing dose. The maximal effect at 480 U resulted in a 75% reduction in M-wave amplitude from baseline.

In a separate study, 10 subjects were randomized to be injected with a dose of botulinum toxin Type B "B" formulation in one EDB and a dose of "BOTOX®" (botulinum toxin Type A, "A") in the other EDB using one of five different dosing schemes: 1.25 UA/20UB; 2.5 UA/80UB; 5 UA/160UB; 7.5 UA/320UB; 10U A/480 U B (2 subjects per dosage schedule). One control subject was given a saline injection in each EDB muscle. The rate of fall in the M-wave amplitude and area was similar in both muscles, with maximal effect occurring at approximately day 6 post injection. Both serotypes exhibited a dose-dependent decrement in M-wave amplitude. Post-exercise facilitation was largest at day 9 for both types of toxin.

While the invention has been described with reference to specific methods and embodiments, it will be appreciated that various modifications and changes may be made without departing from the invention.

The invention claimed is:

1. A stable liquid pharmaceutical botulinum toxin formulation for therapeutic use in humans, comprising
a pharmaceutically acceptable buffered saline comprising a buffering component that is succinate buffer, in which said buffered saline provides a buffered pH range to the formulation between pH 5 and pH 6,
a therapeutic concentration of a purified botulinum toxin suitable for use in humans, and serum albumin;
wherein the formulation is stable as a liquid when stored for at least one year at a temperature of about 5 degrees centigrade or for at least 6 months at a temperature between about 10 and 30 degrees centigrade.

2. The formulation of claim 1, wherein said buffered pH is between about pH 5.4 and pH 5.8.

3. The formulation of claim 1, wherein said formulation is stable in liquid form for at least two years at a temperature of about 5 degrees centigrade.

4. The formulation of claim 1, wherein said botulinum toxin is of a botulinum toxin serotype selected from the group consisting of serotypes A, B, $C_1$, $C_2$, D, E, F and G.

5. The formulation of claim 4, wherein said botulinum toxin is botulinum toxin Type B present at said therapeutic concentration in the range of 100–20,000 U/ml±10%.

6. The formulation of claim 4, wherein said botulinum toxin is botulinum toxin Type A, and is present in the stable liquid pharmaceutical formulation at said therapeutic concentration in the range of between 20–2000 U/ml.

7. The formulation of claim 5, wherein said botulinum toxin Type B is present in a high molecular weight complex of 700 kilodaltons (kD)±10%.

8. The formulation of claim 5, wherein said botulinum toxin Type B is present at said therapeutic concentration between 1000–5000 U/ml.

9. The formulation of claim 6, wherein said botulinum toxin Type A is present in the stable liquid pharmaceutical formulation at said therapeutic concentration in the range of between 100–1000 U/ml.

10. The formulation of claim 1, wherein the stable liquid pharmaceutical formulation comprises 100 mM sodium chloride; 10 mM succinate buffer at a buffered pH of 5.6; 0.5 mg/mL human serum albumin; and botulinum type B present at a concentration of 5,000±1000 U/ml.

11. The formulation of claim 1, wherein said formulation is stable as a liquid for at least one year at a temperature of about 5±3 degrees centigrade.

12. The formulation of claim 1, wherein said formulation is stable as a liquid for at least one year at a temperature of about 4±2 degrees centigrade.

13. A stable liquid pharmaceutical formulation for therapeutic use in humans comprising
0.5 mg/ml human serum albumin,
botulinum toxin type B present at a concentration of 5,000±1000 U/ml, and
a pharmaceutically acceptable buffered saline which provides a buffered pH to the formulation of pH 5.6,
wherein said botulinum toxin is stable in said formulation for at least about 6 months at a temperature between 10 and 30 degrees centigrade±10%, and
wherein said buffered saline comprises 100 mM sodium chloride and 10 mM succinate buffer.

14. A method of treating a patient in need of inhibition of cholinergic input to a selected muscle, muscle group, gland or organ, comprising administering to the selected muscle, muscle group, gland or organ of the patient a pharmaceutically effective dose of the stable liquid pharmaceutical botulinum toxin formulation of claims 1 or 13.

15. The method of claim 14, wherein said patient is suffering from a disorder selected from the group consisting of spasticity, blepharospasm, strabismus, hemifacial spasm, dystonia, otitis media, spastic colitis, animus, urinary detrusor-sphincter dyssynergia, jaw-clenching, and curvature of the spine.

16. The method of claim 14, wherein said selected muscle or muscle group produces a wrinkle or a furrowed brow.

17. The method of claim 14, wherein said muscle is a perineal muscle and wherein said patient is in the process of giving birth to a child.

18. The method of claim 14, wherein said patient is suffering from a condition selected from the group consisting of myofascial pain, headache associated with migraine, vascular disturbances, neuralgia, neuropathy, arthritis pain, back pain, hyperhydrosis, rhinnorhea, asthma, excessive salivation, and excessive stomach acid secretion.

19. The method of claim 14, wherein said formulation is stable as a liquid for at least one year at a temperature of about 5±3 degrees centigrade.

20. The method of claim 14, wherein said formulation is stable as a liquid for at least one year at a temperature of about 4±2 degrees centigrade.

21. The method of claim 14, wherein said formulation is stable as a liquid for at least six months at a temperature of about 25 degrees centigrade.

22. The method of a claim 14, wherein said buffered pH range is between about pH 5.4 and pH 5.8.

23. The method of claim 14, wherein said botulinum toxin is a botulinum toxin serotype selected from the group consisting of serotypes A, B, $C_1$, $C_2$, D, E, F and G.

24. The method of claim 14, wherein said serum albumin is recombinant human serum albumin.

25. The method of claim 14, wherein said patient is refractory to botulinum toxin Type A and said botulinum toxin in said formulation is selected from the group consisting of botulinum serotypes B, $C_1$, $C_2$, D, E, F and G.

26. The method of claim 14, wherein said patient is refractory to botulinum toxin Type B and said botulinum toxin in said formulation is selected from the group consisting of botulinum serotypes A, $C_1$, $C_2$, D, E, F and G.

27. The method of claim 15, wherein said patient is suffering from spasticity due to one or more of the group consisting of stroke, spinal cord injury, closed head trauma, cerebral palsy, multiple sclerosis, and Parkinson's disease.

28. The method of claim 15, wherein said patient is suffering from a dystonia selected from the group consisting of spasmodic torticollis (cervical dystonia), spasmodic dyshponia, limb dystonia, laryngeal dystonia, and oromandibular (Meige's) dystonia.

29. The method of claim 23, wherein said botulinum toxin is botulinum toxin Type B present at a concentration in the range of about 100–20,000 U/ml.

30. The method of claim 23, wherein said botulinum toxin is botulinum toxin Type A, present at a concentration in the range of about 20–2000 U/ml.

31. The method of claim 25, wherein said botulinum toxin in said formulation is botulinum toxin Type B.

32. The method of claim 26, wherein said botulinum toxin in said formulation is botulinum toxin Type A.

33. The method of claim 29, wherein said botulinum toxin Type B is present in a high molecular weight complex of about 700 kD.

34. The method of claim 29, wherein said botulinum toxin Type B is present at a concentration of about 1000–5000 U/ml.

35. The method of claim 30, wherein said botulinum toxin Type A is present at a concentration in the range of about 100–1000 U/ml.

\* \* \* \* \*